United States Patent [19]

Izawa et al.

[11] Patent Number: 4,556,639
[45] Date of Patent: Dec. 3, 1985

[54] METHOD AND APPARATUS FOR DISLODGING CULTURED CELLS

[75] Inventors: Masao Izawa; Sachiko Tatsukawa, both of Tokyo, Japan

[73] Assignee: Olympus Optical Co., Ltd., Tokyo, Japan

[21] Appl. No.: 472,286

[22] Filed: Mar. 4, 1983

[30] Foreign Application Priority Data

Mar. 15, 1982 [JP] Japan .................................. 57-40486

[51] Int. Cl.[4] ........................ C12M 3/00; C12M 1/00; C12M 1/02; B01F 11/00
[52] U.S. Cl. .................................... 435/284; 435/287; 435/316; 366/240
[58] Field of Search ................. 435/284–287, 435/316; 366/108, 111, 112, 114, 115, 219, 240

[56] References Cited

U.S. PATENT DOCUMENTS 4,339,537 7/1982 Sogi et al. ........................ 435/285 X

FOREIGN PATENT DOCUMENTS 0063744 11/1982 European Pat. Off. ............ 435/316

Primary Examiner—Robert J. Warden
Assistant Examiner—Shawn P. Foley
Attorney, Agent, or Firm—Frishauf, Holtz, Goodman & Woodward

[57] ABSTRACT

A method for dislodging cultured cells has the steps of preparing a culture container which has a growing surface on which cultured cells are grown, and which is filled with a culture solution in contact with the cultured cells, supporting the culture container on a pedestal to be reciprocally movable in a direction parallel to the growing surface, and reciprocally moving the culture container in the direction parallel to the growing surface and thus applying an inertial force on the cultured cells in the direction parallel to the growing surface, thereby dislodging the cultured cells from the growing surface. An apparatus for dislodging cultured cells has the pedestal for supporting the culture container and a reciprocating device for reciprocally moving the culture container supported on the pedestal in the direction parallel to the growing surface.

15 Claims, 6 Drawing Figures

METHOD AND APPARATUS FOR DISLODGING CULTURED CELLS

BACKGROUND OF THE INVENTION

The present invention relates to a method and an apparatus for recovering separated cultured cells.

Techniques for culturing living organisms and cells are known as basic experimental techniques to assist cytological studies in the fields of medicine, biology, pharmacology, agriculture and the like. Subculture of organisms and cells utilizing such techniques is generally performed according to the following procedures.

A culture solution in a culture container in which cells have been cultured is discharged therefrom, leaving the cultured cells behind. A buffer is poured into the container to rinse the cell surfaces, and the buffer is then also discharged. Subsequently, an enzyme solution containing a proteinase is poured into the container. After the container has been left to stand for 1 minute, the enzyme solution is discharged, and the container is left to stand for a further period of 5 to 10 minutes. Fresh culture solution is then poured into the container and stirred so as to remove therefrom the cultured cells attached to the bottom surface of the container, and to separate them from each other. The culture solution containing separated cells is then poured into other culture containers for further multiplication.

In a series of culture procedures as described above, the steps of dislodging the cells from the bottom of the container by stirring, and of pouring the fresh culture solution into other culture containers, most affect the subsequent growth of the cultured cells. These steps are the most important factors in determining the recovery rate of the cells, the degree of subsequent cell attachment, damage to the cell membranes, and so on. For these reasons, these are the most important steps in subculture techniques.

Removal of the cells from the growing surface of the container is conventionally performed by the following method. First, a lid of a culture container such as a petri dish is opened. The culture solution in the petri dish is repeatedly drawn and discharged with a pipette so as to remove the cultured cells attached to the growing surface or bottom surface of the petri dish, and to separate the cells from each other. When this method is performed manually, the pipette may be freely moved or pivoted so as to remove the cells uniformly. However, when the method is performed automatically with a machine, various problems are encountered. For example, an apparatus is known which draws and discharges the culture solution by moving the distal end of a pipette to and fro. However, with this apparatus, the range of the growing surface from which the cells are removed is limited, resulting in irregular cell removal. In order to prevent irregular cell removal, the petri dish may be rotated or the delivery rate of the pipette may be increased. However, the structure of the apparatus becomes complex with the former measure, while the culture solution may be spilt outside the petri dish with the latter measure. Furthermore, an apparatus for removing the cells with a pipette requires a long time for complete removal. In addition, the removal procedure is performed with the lid of the petri dish open, so that the cultured cells and culture solution are easily subject to contamination.

Another method for removing cultured cells from a growing surface is known in which an impact is repeatedly applied to a culture container in a direction perpendicular to the growing surface. FIG. 1 shows an apparatus for practicing this method. The apparatus has a support frame 100 of an L-shaped cross-section, an annular base 102 mounted on the support frame 100, and a platform 104 mounted on the annular base 102. A pair of solenoids 106 and 108 are mounted on the support frame 100 and below the platform 104, and have plungers 110 and 112, respectively, which project toward the lower surface of the platform 104. The solenoids 106 and 108 are connected to a drive circuit 114. The drive circuit 114 supplies a pulsed drive current to drive these solenoids 106 and 108. A mounting member 116 is fixed on the upper end of the support frame 100. A buffer member such as a coil spring 118 is mounted to the mounting member 116 so as to oppose the platform 104.

A case in which the cultured cells are removed using the apparatus of the construction as described above will now be described. A petri dish 120 as a culture container is prepared. Cultured cells 122 are attached to the bottom surface of the petri dish 120, and a culture solution 124 is held in the petri dish 120. The petri dish 120 is subjected to the following operations: discharge of the used culture solution, pouring and discharge of a buffer, pouring and discharge of an enzyme solution, and pouring of a fresh culture solution. Thereafter, a lid 126 of the petri dish 120 is closed and the petri dish 120 is placed on the platform 104. The lid 126 is pressed downward by the buffer member 118 so that the petri dish 120 is securely held on the platform 104. A pulsed drive current from the drive circuit 114 is alternately supplied to the solenoids 106 and 108. Then, the plungers 110 and 112 alternately strike or impact against the bottom wall of the petri dish 120 through the platform 104. Since the petri dish 120 is elastically held by the buffer member 118, accidental opening of the lid 126 and resultant spillage of the culture solution may be prevented. Slippage of the petri dish 120 from the platform 104 is also prevented. Accordingly, the petri dish 120 is struck a sufficient number of times. The petri dish 120 is repeatedly struck for about 1 minute to completely dislodge all the cultured cells from the growing surface or the bottom surface of the petri dish 120.

However, when the cultured cells are removed by the method and apparatus as described above, more than one solenoid must be used, making the apparatus complicated. Control for alternately energizing the solenoids is difficult. The impacts acting upon the growing surface in the direction perpendicular thereto do not effectively dislodge the cells from the growing surface. For this reason, the cell removal rate largely depends upon the effectiveness of other steps such as enzyme treatment. For example, if the enzyme treatment is insufficient and dissolution of the cytoplasm bonding the cells to the growing surface is insufficient, the cell removal rate is significantly degraded. Furthermore, since the impacts act upon the bottom wall of the petri dish 120 which is relatively weak, damage to the petri dish 120 and the cells contained therein may be easily caused. Although the degree of difficulty in cell removal may vary depending upon the condition of the cells, in particular, the age of the cells, the apparatus fails to allow free selection of the frequency or magnitude of the impacts to be applied.

SUMMARY OF THE INVENTION

The present invention has been made in consideration of this and has for its object to provide a method for easily dislodging cultured cells from a culture container without damaging the container or the cells; and to provide an apparatus which allows free selection of the operation mode in accordance with the condition of the cells involved, and which is simple in construction.

According to an aspect of the present invention, there is provided a method for dislodging cultured cells, comprising: a step of preparing a culture container into which cultured cells are implanted and grown on a growing surface thereof, a step of supporting the culture container on a supporting means to be reciprocally movable in the direction parallel to the growing surface, and a step of reciprocally moving the culture container in the direction parallel to the growing surface and thus applying an inertia force on the cultured cells in the direction parallel to the growing surface, thereby dislodging the cultured cells from the growing surface.

According to the method of the present invention, an inertia force acts on the cultured cells in the direction parallel to the growing surface. For this reason, the cells may be readily dislodged from the growing surface, the recovery rate of the cells may be improved, and the cells are least subject to damage. Reciprocal movement of the culture container in the direction parallel to the growing surface may be easily accomplished by a single pair of a plunger and a solenoid. The apparatus for practicing this method may be simple in construction allowing easy control of the reciprocal movement of the container. In particular, when a petri dish is used as a culture container and the bottom surface of the dish serves as a growing surface, with the method of the present invention the bottom wall of the dish is not subjected to impact, unlike the conventional method. Damage to the petri dish and hence to the cells may thus be prevented.

BRIEF DESCRIPTION OF THE DRAWINGS

FIGS. 2 to 4 show a dislodging apparatus according to an embodiment of the present invention, wherein FIG. 2 is a partially broken side view of the apparatus, FIG. 3 is a perspective view of a striking member and a culture container, and FIG. 4 is a sectional view of a pedestal and the culture container.

DETAILED DESCRIPTION OF THE PREFERRED EMBODIMENT

Figure 2:
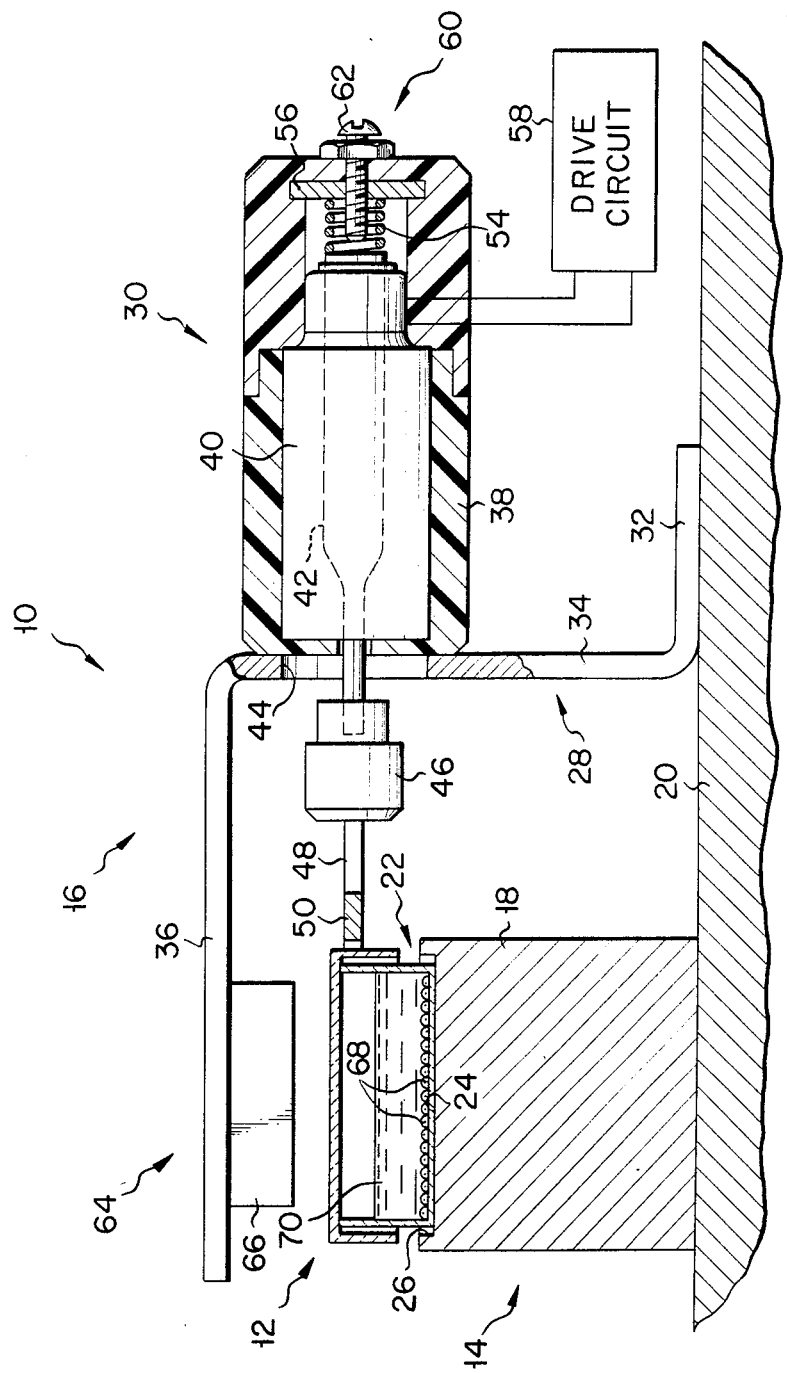

A dislodging apparatus for practicing the method of the present invention will first be described. Referring to FIG. 2, a dislodging apparatus 10 has a supporting means 14 supporting a petri dish 12 as a culture container thereon, and a reciprocating means 16 for reciprocating the petri dish 12. The supporting means 14 has a columnar pedestal 18. The pedestal 18 is fixed to a base 20, and has in its top surface a recess 22 for receiving the petri dish. The recess 22 has a circular shape, and includes a circular support surface 24 and a side surface 26. The support surface 24 is substantially horizontal and has a diameter slightly greater than that of the bottom wall of the petri dish 12. The side surface 26 is substantially perpendicular to support surface 24 and is adapted to be abuttable against the lower portion of the peripheral wall of the petri dish 12, and defines a repulsing means of the reciprocating means 16 as will be described later. The petri dish 12 is placed on the recessed support surface 24 so that it may not drop from the pedestal 18 and so that it is horizontally movable for a short distance. In other words, the petri dish 12 is supported to be slightly movable in the direction parallel to the growing surface or bottom surface thereof.

The reciprocating means 16 includes a support member 28 fixed to the base 20, and a striking means 30 fixed to the support member 28 to tap or strike the petri dish 12. The support member 28 includes a plate which is bent in the form of a crank. The support member 28 has a stationary part 32 fixed to the base 20, a vertical part 34 which vertically extends from the stationary part 32 above the base 20 and which opposes the pedestal 18, and a horizontal part 36 which extends horizontally from the upper end of the vertical part 34 toward a position above the pedestal 18. The striking means 30 is mounted on the vertical part 34 of the support member 28.

Figure 1:
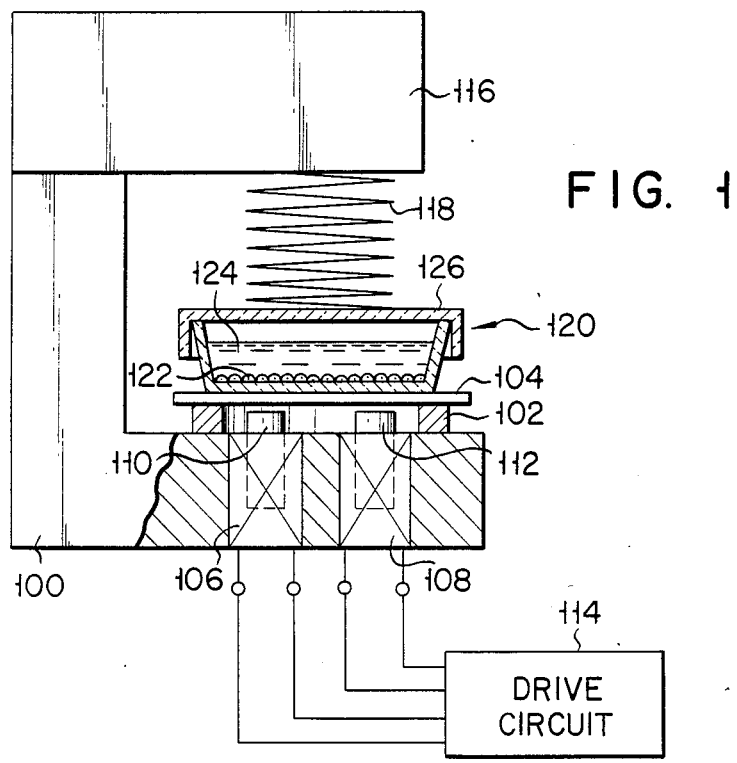
FIG. 1 is a partially broken front view of a conventional dislodging apparatus.
Figure 3:
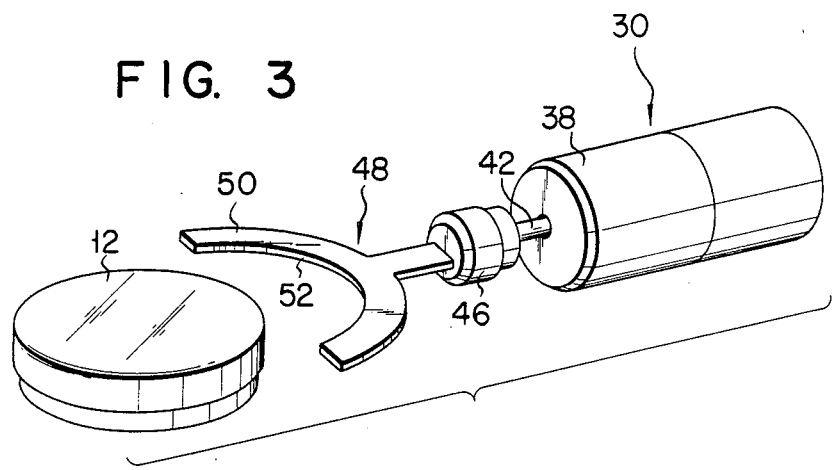

As shown in FIGS. 2 and 3, the striking means 30 includes a watertight case 38 mounted on the vertical part 34, a solenoid 40 housed in the case 38, and a plunger 42 which is arranged inside the solenoid and which is movable horizontally, that is, in the direction parallel to the support surface 24. The distal end of the plunger 42 extends toward the petri dish 12 through the case 38 and a through hole 44 formed in the vertical part 34. A striking member 48 is detachably mounted on the distal end of the plunger 42 through a connecting member 46. As may be seen from FIG. 3, the striking member 48 has a contact portion 50 which may contact the petri dish 12. The contact portion 50 is branched to have a semicircular contact edge 52 which may contact the peripheral wall of the petri dish 12. The striking member 48 is movable together with the plunger 42 in the direction parallel to the growing surface or bottom surface of the petri dish 12. A compression spring 54 is housed inside the watertight case 38. One end of the compression spring 54 is fixed to the rear end of the plunger 42, while the other end thereof is fixed to a spring receiver 56 inside the case 38. A drive circuit 58 is connected to the solenoid 40 and supplies a pulsed drive current to the solenoid to drive the plunger 42. In the state where the compression spring 54 is neither compressed nor expanded, that is, in the normal state where the solenoid 40 is not driven by the drive circuit 58, the contact portion 50 of the striking member 48 rests adjacent to the peripheral wall of the petri dish 12 placed on the support surface 24 of the pedestal 18. In general, cells are cultured in a 100% humidity atmosphere. Therefore, the watertight case 38 serves to protect the solenoid 40 against moisture.

The striking means 30 has an adjusting means 60 for adjusting the operating range, that is, the range of horizontal movement, of the plunger 42. The adjusting means 60 has an adjusting screw 62 which extends through the watertight case 38 and the spring receiver 56 and is screwed into the case 38 from its rear side. The adjusting screw 62 extends horizontally inside the compression spring 54, and the distal end of the screw opposes at a predetermined distance the rear end surface of the plunger 42. The operating range of the plunger 42 may be adjusted by rotating the screw 62 so as to change the predetermined distance between the distal end of the screw 62 and the rear end surface of the plunger 42. When the operating range of the plunger 42 is changed, the strength of the impact applied upon the petri dish 12 through the striking means 48 is adjusted.

The reciprocating means 16 has a fall preventing means 64 for preventing the petri dish 12 from accidentally falling from the pedestal 18. The fall preventing means 64 has a fall preventing member 66 which is mounted on the horizontal part 36 of the support member 28 to be located above the pedestal 18. The fall preventing member 66 is disc-shaped and is made of rubber, plastic or the like. The fall preventing member 66 opposes at a short distance the petri dish 12 placed in the recess 22. When the petri dish 12 is struck by the striking member 48, the fall preventing member 66 prevents the lid of the petri dish 12 and the petri dish 12 itself from accidentally falling from the pedestal 18.

The mode of operation of the dislodging apparatus 10 of the construction as described above will now be described together with the dislodging method of the present invention.

A petri dish 12 is prepared as a culture container. Cultured cells 68 are implanted and grown on the growing surface or bottom surface of the petri dish 12. A culture solution 70 is also contained in the petri dish 12. The culture solution in the petri dish 12 which has been used to grow the cells 68 is discharged. A buffer is then poured into the petri dish 12 to clean the cell surfaces, and the buffer is discharged. An enzyme solution containing a proteinase is then poured into the petri dish 12 so as to dissolve the cytoplasm bonding the cultured cells and the growing surface together. After discharging the enzyme solution, fresh culture solution is poured into the petri dish 12.

Figure 4:
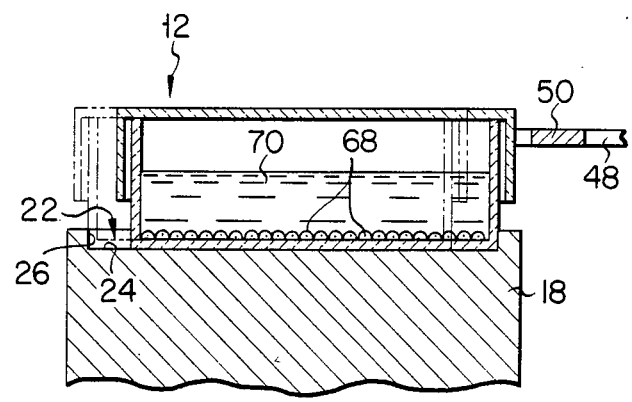

After the above procedures have been completed, the petri dish 12 is placed on the support surface 24 of the pedestal 18. A pulsed drive current from the drive circuit 58 is supplied to the solenoid 40. Then, the plunger 42 is drawn into the solenoid 40 against the biasing force of the compression spring 54 until its rear end surface abuts against the distal end of the adjusting screw 62. When the solenoid 40 in this state is deenergized, the plunger 42 is moved to the left (in FIG. 2) so as to be ejected from the solenoid 40 by the biasing force of the compression spring 54. Then, the plunger 42 is restored to the position where the compression spring 54 is neither compressed nor expanded, so that it may not act thereon. After the plunger 42 reaches such a position, the plunger 42 further moves to the left against the biasing force of the compression spring 54 by its own inertia. Then, the contact edge 52 of the striking member 48 is pushed against the peripheral wall of the lid of the petri dish 12 to strike it. In this manner, the petri dish 12 is subjected to a force acting in the direction parallel to the growing surface or bottom surface thereof, so that it is pushed along the support surface 24 from the position indicated by the solid line to the position indicated by the two dot-and-dash line in FIG. 4. When the petri dish 12 is pushed to the position indicated by the two dot-and-dash line, the lower portion of its peripheral wall bumps against the side surface 26 of the recess 22. Thus, the petri dish 12 is subjected to an impact acting in the substantially opposite direction from the initial impact, by reaction, and is returned to the position indicated by the solid line. As has been described earlier, the side surface 26 of the recess 22 thus constitutes a repulsing means for causing the petri dish 12 to rebound. When the striking member 48 strikes the petri dish 12, the plunger 42 is drawn inside the solenoid 40 by the biasing force of the compression spring 54 and is returned to the normal position. When the plunger 42 returns to the normal position in this manner, a pulsed drive current is supplied to the solenoid 40 to repeat the operation as described above. As the solenoid 40 is continuously energized with a pulsed drive current having a suitable period, the plunger 42 periodically reciprocates with this period. Then, the striking member 48 strikes the petri dish 12 when the plunger 42 reaches its leftmost position, and the petri dish 12 repeats its reciprocal movement within the recess 22.

When the petri dish 12 is reciprocated in the direction parallel to its growing surface by the reciprocating means 16, the cultured cells 68 are subjected to inertia force acting in the direction parallel to the growing surface by the abrupt change in the direction of movement of the petri dish 12. When the reciprocal movement of the petri dish 12 is repeated a plurality of times, the cultured cells 68 which have been treated with an enzyme may be reliably dislodged from the growing surface. Supply of current to the solenoid 40 from the drive circuit 58 is interrupted to terminate the operation of the dislodging apparatus 10.

According to the method of the present invention as described above, the petri dish 12 is reciprocated in the direction parallel to its growing surface, and the cultured cells 68 are dislodged as inertia force acts on them in the direction parallel to the growing surface. Thus, the cultured cells 68 may be efficiently dislodged from the growing surface while allowing an improvement in the recovery rate of the cells and prevention of damage thereto.

The striking means 30 has the adjusting screw 62 which allows the range of movement of the plunger 42, and hence, of the striking member 48, to be adjusted. Therefore, the magnitude of each strike against the petri dish 12 may be freely adjusted by means of the adjusting screw 62. Furthermore, the period (frequency) of the strike against the petri dish 12 by the striking member 48 may be adjusted by changing the energization period of the drive current supplied from the drive circuit 58 to the solenoid 40. The magnitude and frequency of the strikes to be applied to the petri dish 12 may be decreased if the cultured cells 68 are easy to dislodge; that is, if the cultured cells 68 are young, have not been grown for many days after being grown in a monolayer, or have been subjected to sufficient enzyme treatment. On the other hand, the magnitude and frequency of the strikes to be applied to the petri dish 12 may be increased if the cultured cells 68 are hard to remove; that is, if the cultured cells 68 are old, have propagated too much so as to crowd the container, or have been subjected to insufficient enzyme treatment. In this manner, the magnitude and frequency of the strikes may be freely adjusted in accordance with the differing conditions of the cultured cells 68. Furthermore, the striking means 30 has a simple construction incorporating only a single pair of a solenoid 40 and a plunger 42.

Figure 5:
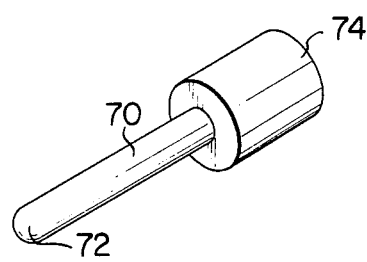
FIGS. 5 and 6, respectively, are perspective views showing modifications of the striking member.

The above embodiment has been described and illustrated only for the purpose of easy understanding and the present invention is not limited to this particular embodiment. For example, the striking member 48 need not be limited to that used in the above embodiment, but one shown in FIG. 5 or 6 may also be used. A striking member 70 shown in FIG. 5 has an overall columnar shape and has a rounded contact end 72. The striking member 70 can apply a relatively light impact to the petri dish 12 and may be conveniently used for removing epitheloids or young fibroblasts which are relatively easy to remove.

Figure 6:
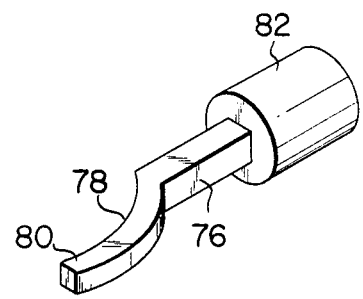

A striking member 76 shown in FIG. 6 has a contact portion 80, with a contact edge 78, of ¼ circular shape. When an impact is applied to the petri dish 12 by this striking member 76, the petri dish 12 receives the impact while its peripheral wall is rubbed by the striking member. Therefore, the petri dish 12 is reciprocated while being rotated within the recess 22. As a result, the striking force acts uniformly on the entire peripheral wall of the petri dish 12, so that the cultured cells 68 are uniformly removed. The striking member 76 shown in FIG. 6 may therefore be conveniently used for dislodging old cells which are relatively hard to remove. The striking member 70 or 76 is detachably mounted on the plunger 42 through engagement of the distal end of the plunger into a mount hole (not shown) formed in a connecting member 74 or 82, respectively.

In the above embodiment, the reciprocating means 16 has the striking means 30 and the repulsing means, that is, the side surface 26 of the recess 22. However, the present invention is not limited to this. For example, the petri dish 12 may be reciprocated by the reciprocating means 16 without using a repulsing means if the contact portion of the striking member 48 has an annular shape that is fitted around the peripheral wall of the petri dish 12. The fall preventing means 64 is not limited to the disc-shaped fall preventing member 66 but may be a spring.

What we claim is:

1. A method for dislodging cultured cells, comprising:
preparing a culture container which has a growing surface on which cultured cells are grown, treating the cultured cells with an enzyme solution, and filling the culture container with a culture solution to contact with the cultured cells;
supporting the culture container on supporting means so as to be reciprocally movable in a direction parallel to the growing surface;
applying an impact to the culture container by striking means to move the culture container in one direction parallel to the growing surface; and
bumping the culture container moving in said one direction against repulsive means to move the culture container in a direction opposite to said one direction, thereby applying an inertia force on the cultured cells in the direction parallel to the growing surface and dislodging the cultured cells from the growing surface.

2. A method according to claim 1, wherein said step of preparing includes processes of discharging used culture solution from the culture container, pouring a buffer into the culture container and of rinsing the cultured cells with the buffer, discharging the buffer from the culture container, pouring an enzyme solution containing a lytic enzyme into the culture container and of dissolving a cytoplasm bonding the growing surface and the cultured cells, discharging the enzyme solution from the culture container, and pouring a fresh culture solution into the culture container.

3. An apparatus for disloding cultured cells from a growing surface of a culture container in which the cells have been implanted and grown on the growing surface and which also contains a culture solution in contact with the cultured cells, comprising:

supporting means for supporting a culture container to be reciprocally movable in a direction parallel to the growing surface; and
reciprocating means for reciprocally moving the culture container supported by the supporting means in the direction parallel to the growing surface so that an inertia force acts on the cultured cells in the direction parallel to the growing surface to dislodge the cultured cells from the growing surface;
said reciprocating means including striking means for applying an impact to the culture container supported by the supporting means in the direction parallel to the growing surface to move the culture container in one direction; and
said supporting means including repulsive means for repelling the culture container moving in said one direction to move the culture container in a direction substantially opposite to said one direction.

4. An apparatus according to claim 3, wherein said striking means has a solenoid, a drive circuit connected to the solenoid to supply a drive current to the solenoid, a plunger which is arranged inside the solenoid to be reciprocally movable in the direction parallel to the growing surface and which is driven by the solenoid, a striking member which is detachably mounted on one end of the plunger to be movable together with the plunger and which is adapted to strike the culture container supported by the supporting means, and biasing means for biasing the plunger against the culture container supported by the supporting means.

5. An apparatus according to claim 4, wherein said striking means has adjusting means for adjusting a range of movement of the plunger to adjust the impact to be applied to the culture container.

6. An apparatus according to claim 5, wherein said supporting means has a pedestal having a recess for receiving the culture container therein, the recess having a supporting surface and a side surface, the supporting surface supporting the culture container to allow the culture container to reciprocate for a short distance in the direction parallel to the growing surface, the side surface being arranged substantially perpendicular to the supporting surface and being adapted to contact the culture container, and the side surface constituting the repulsing means.

7. An apparatus according to claim 6, which further comprises a base supporting the pedestal and wherein the reciprocating means has a support member mounted on the base and supporting the striking means thereon, the support member having a vertical part and a horizontal part, the vertical part being opposed to the pedestal and supporting the striking means thereon, and the horizontal part extending from the vertical part to a position above the recess of the pedestal.

8. An apparatus according to claim 7, which further comprises fall preventing means for preventing the culture container placed on the pedestal from falling therefrom.

9. An apparatus according to claim 8, wherein said fall preventing means comprises a fall preventing member which is made of an elastic material and which is mounted on the horizontal part of the support member to be located at a position above the recess and to be opposed thereto.

10. An apparatus according to claim 4, wherein said striking member has a contact portion which has a semicircular contact edge adapted to strike the culture container supported by the supporting means.

11. An apparatus according to claim 4, wherein said striking means has a contact portion which has a rounded contact edge adapted to strike the culture container supported by the supporting means.

12. An apparatus according to claim 4, wherein said striking member has a contact portion which has a contact edge of a ¼ circular shape and adapted to strike the culture container supported by the supporting means.

13. An apparatus according to claim 5, wherein said striking means has a watertight case housing the solenoid therein.

14. An apparatus according to claim 13, wherein said biasing means has a compression spring which has one end fixed to the other end of the plunger and the other end fixed to the watertight case and which is housed in the watertight case.

15. An apparatus according to claim 14, wherein said adjusting means has an adjustment screw a distal end of which is screwed into the watertight case through the compression spring and is opposed to the other end of the plunger, the range of movement of the plunger being adjustable by varying a degree of screwing of the adjusting screw to change a distance between the distal end of the adjusting screw and the other end of the plunger.

* * * * *